United States Patent [19]

Haeger

[11] Patent Number: 5,173,488

[45] Date of Patent: Dec. 22, 1992

[54] STABLE INJECTABLE PHARMACEUTICAL FORMULATION FOR FOLIC ACID AND LEUCOVORIN SALTS AND METHOD

[75] Inventor: Bruce E. Haeger, Highland Mills, N.Y.

[73] Assignee: American Cyanamid Company, Stamford, Conn.

[21] Appl. No.: 696,335

[22] Filed: May 1, 1991

Related U.S. Application Data

[63] Continuation of Ser. No. 396,573, Aug. 21, 1989, abandoned.

[51] Int. Cl.$^5$ ............... A61K 31/505; A61K 47/10; A61K 47/20; A61K 47/18
[52] U.S. Cl. ............................ 514/249; 514/973; 544/258
[58] Field of Search ............... 514/249, 973; 544/258

[56] References Cited

U.S. PATENT DOCUMENTS

| | | | |
|---|---|---|---|
| 1,926,797 | 9/1933 | Sutton | 514/706 |
| 2,688,018 | 8/1954 | Cosulich | 544/258 |
| 2,695,860 | 11/1954 | Weidenheimer et al. | 544/258 |
| 2,741,608 | 8/1956 | Shive | 544/258 |
| 3,696,195 | 10/1972 | Crivellaro et al. | 514/973 |
| 4,071,620 | 1/1978 | Sklar | 424/175 |
| 4,500,711 | 2/1985 | Wisowaty et al. | 544/258 |
| 4,931,441 | 6/1990 | Lawrence | 514/249 |

FOREIGN PATENT DOCUMENTS

WO88/04927 7/1988 PCT Int'l Appl.

OTHER PUBLICATIONS

Physicians Desk Reference (Oradell, N.J., Medical Economics Co., 1988) pp. 1148–1152.
Durst, et al. Clinical Chemistry 18, (3) 1972, pp. 206–208.
United States Pharmacopeia, XX, 1980, pp. 832–833, and 1237.

Primary Examiner—Robert T. Bond
Attorney, Agent, or Firm—Thomas S. Szatkowski

[57] ABSTRACT

Injectable aqueous compositions comprising folic acid and leucovorin and their salts, optionally including benzyl alcohol, sodium chloride and agents for adjusting pH are stabilized and buffered in the range of 6 to 10 by adding a combination of tromethamine and monothioglycerol. Such compositions remain stable for prolonged periods even when exposed to sunlight.

20 Claims, No Drawings

STABLE INJECTABLE PHARMACEUTICAL FORMULATION FOR FOLIC ACID AND LEUCOVORIN SALTS AND METHOD

This is a continuation of copending application Ser. No. 07/396,573 filed on Aug. 21, 1989, now abandoned.

The present invention relates to new improved injectable compositions comprising folic acid salts and leucovorin salts. More particularly, it relates to compositions comprising folic acid salts and leucovorin salts that remain stable for prolonged periods under normal storage conditions because they include tromethamine and monothioglycerol as a buffering agent/antioxidant combination.

BACKGROUND OF THE INVENTION

Folic acid and its salts and leucovorin and its salts are known to be pharmaceutically effective. See, Remington's Pharmaceutical Sciences, Seventeenth Edition, Mack Publishing Co., Easton, PA 1985 (Remington's 17th Ed.) p. 1023. Folic acid is used to treat vitamin deficiencies. Cosulich, U.S. Pat. No. 2,688,018 describes the preparation of such compounds and their clinical use for controlling the toxicity of aminopterin and other antifolic acid compounds and as hematopoietic drugs. Active derivatives of such compounds are described in Shive, U.S. Pat. No. 2,741,608. In U.S. Pat. No. 4,500,711, Wisowaty et al., describe the purification of leucovorin and its salts. Kerwar et al., U.S. Pat. No. 4,746,662 disclose that the antiarthritic efficacy of methotrexate can be potentiated by injection of an aqueous solution of leucovorin or its salts. EPO Patent Publication No. 0,266,042, May 4, 1988, describes using pure leucovorin isomers to manufacture medicaments for methotrexate rescue, for treatment of colorectal cancer in combination with 5-fluorouracil, and for treating folate deficiency.

Both folic acid and leucovorin are only sparingly soluble in water. Therefore they are administered in the form of salts such as alkaline metal and alkaline earth metal salts, such as the sodium salt of folic acid and the calcium salt of leucovorin, the 1-isomer of the latter being preferred.

The compound N-4-((2-Amino -1,4-Dihydro-4-oxo-6-pteridinyl)methyl) -amino)(benzoyl)-L-glutamic acid, sodium salt (Sodium Folate) having the formula

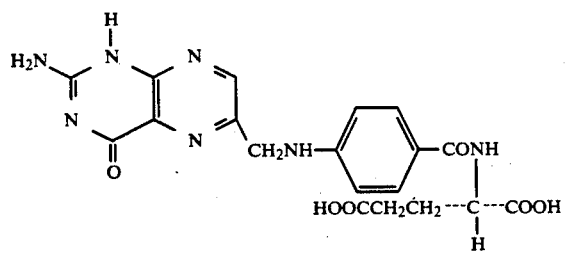

is used principally to stimulate specifically the production of red blood cells, white blood cells and platelets in persons suffering from certain megaloblastic anemias.

The compound N-(4-((2-Amino-5-formyl -1,4,5,6,7,8-hexahydro-4-oxo-6-pteridinyl)methyl)amino)benzoyl)-L-glutamic acid, calcium salt (1:1), pentahydrate, (Leucovorin Calcium USP) having the formula:

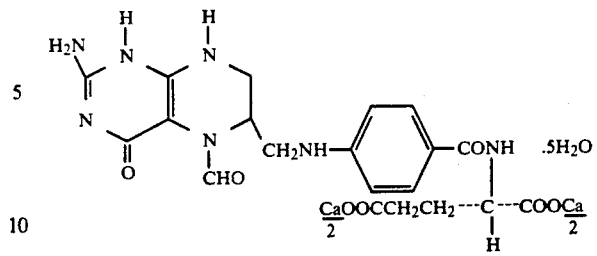

is used principally as an antidote for folic acid antagonists such as methotrexate, which block the conversion of folic acid into folinic acid. Merck Index, Tenth Edition, p. 603. Both folic acid and leucovorin salts are formulated in water for injection and may contain suitable preservatives, as described under Folvite ® Injection and Leucovorin Calcium Injection in the Physician's Desk Reference, Medical Economics Company, Oradell, NJ 1989 (PDR) pp. 1120 and 1124, respectively.

Both compounds, but especially Leucovorin Calcium, require an alkaline pH of 7.7-8.2 for maximum stability. They are also light sensitive and prone to oxidative degradation in aqueous solution, thus requiring the use of amber glass for protection against photosensitivity and the use of nitrogen gas as a protectant throughout the bulk liquid manufacturing process and as a package headspace gas.

In the past, methyl and propyl parabens (p-hydroxy benzoates) were used as a preservative for such salts, especially Leucovorin Calcium Injection. However, the parabens were later found to have short term effectiveness at the alkaline pH required for maximum folic acid and/or leucovorin stability. Subsequently, benzyl alcohol was approved and widely used as the new preservative for the products. See "Folvite ® Folic Acid Solution" and "Leucovorin Calcium Injection", PDR, pp. 1120 and 1124 respectively. Although benzyl alcohol is effective as a preservative, it lacks the mild buffering activity afforded by the parabens. As a consequence the pH of the products tend to be somewhat unstable, slowly drifting downward with time toward pH 6.5-7.0. This is below the above-mentioned optimum range and may require expiration dating to be very short term.

It has now been found that the factors of pH drift, nitrogen headspace variability and short term expiry dating can be overcome in accordance with this invention by using a buffer/antioxidant combination. The buffer comprises 2-Amino-2-(hydroxymethyl)-1, 3-propanediol, also known as tromethamine. The antioxidant comprises 3-Mercapto-1,2-propanediol, also known as monothioglycerol.

Both compounds, tromethamine and monothioglycerol, are toxicologically acceptable, and are described in U.S. Pharmacopeia XXI, U.S. Pharmacopeial Convention, Rockville, MD 1985 (U.S.P. XXI) at pages 1102 and 1580, respectively.

Surprisingly, the new buffer/antioxidant compositions of the present invention, for tromethamine and monothioglycerol, have been found to be superior to the presently used formulations, in terms of ability to control pH in the desired region of folic acid and leucovorin stability, and in their ability to retard oxidation, and therefore degradation, in sealed dosage forms. These new buffer/antioxidant compositions make it possible to extend the expiry dating of the product and provide the potential for development of a broader dosage line for such products, e.g. single or multi-dose vials containing greater volumes and higher concentrations of either folic acid or leucovorin salts than the present single dose (3-5 mg/ml) ampuls, such as a 10 mg/ml, 100 mg/vial dosage preparation. Unexpectedly also, benzyl alcohol becomes an optional ingredient and this is desirable expecially in cases where large doses are needed in emergencies and too much benzyl alcohol is not recommended.

SUMMARY OF THE INVENTION

According to the present invention there are provided stable, injectable aqueous compositions comprising (i) an effective amount of water-soluble pharmaceutically-acceptable salt of folic acid or leucovorin; optionally, (ii) a small, effective preservative amount of benzyl alcohol; and (iii) an effective amount of a buffer/antioxidant combination comprising (a) tromethamine and (b) monothioglycerol, said combination (iii) being present in an amount at least sufficient to maintain the pH of said composition in a predetermined range of from about 6 to about 10 and to protect the composition against degradation induced by oxygen or light.

In preferred embodiments, the compositions comprise those wherein said salt comprises a salt of dl-leucovorin; those wherein the compositions also include (iv) sodium chloride in an amount sufficient to render said composition isotonic; those which also include (v) a pH adjustor comprising an acid or a base in amount sufficient to adjust the pH to any value within said range; those wherein said pH adjustor comprises hydrochloric acid or sodium hydroxide. Especially preferred are compositions wherein said l-leucovorin salt comprises calcium leucovorin. Special mention is made of a formulation comprising from 3 mg/ml to 25 mg/ml of calcium leucovorin in an isotonic solution at a pH of from 6.5 to 8.5, with or without benzyl alcohol at a concentration of from 0.0% w/v to 0.909% w/v, TRIS (tromethamine) at a concentration of from 0.10% w/v to 0.30% w/v, monothioglycerol at a concentration of from 0.10% w/v to 0.30% w/v; sodium chloride at a concentration from 0.45% to 0.65% w/v, with hydrochloric acid at a concentration of from 5.0 v/v% to 10.0 v/v% and sodium hydroxide at a concentration of from 1.0 w/v% to 5.0 w/v% added as required to adjust the pH; and particularly those in which the concentration of calcium leucovorin on the one hand is 3.0 mg to 3.54 mg/ml and 10 mg to 11 mg/ml, on the other, and the concentrations of benzyl alcohol, TRIS (tromethamine), monothioglycerol and sodium chloride are from 0.765% w/v to 1.035% w/v, 0.150% w/v, 0.200% w/v and 0.560% w/v, respectively.

The present invention also contemplates a method for stabilizing compositions as above defined comprising adding thereto an effective amount of the buffer/antioxidant combination comprising tromethamine and monothioglycerol.

DETAILED DESCRIPTION OF THE INVENTION

The injectable composition of this invention can be prepared by techniques well known to those skilled in the art of pharmaceutical formulation. The substantially pure salts may be prepared, mixed with the other components, filtered, filled into containers, and sealed under aseptic conditions.

Folic acid and its salts can be prepared by any convenient method, for example 2,3-dibromopropionaldehyde, dissolved in a water miscible organic solvent (alcohol, dioxane), is added to a solution of equal molecular quantities of 2,4,5-triamino-6-hydroxypyrimidine and p-aminobenzylglutamic acid, maintaining a pH of about 4 by the controlled addition of alkali as the reaction progresses. If sodium hydroxide is used as the alkali, sodium folate is obtained. To make calcium leucovorin, folic acid is, for example simultaneously hydrogenated and formulated in 90 to 100% formic acid under the influence of platinum oxide catalyst to yield leucovorin. Conversion to the calcium salt may be accomplished by dissolving the leucovorin in sodium hydroxide solution, treating the calcium chloride, and precipitating with ethanol.

Benzyl alcohol is an item of commerce and, if used, is widely available from a number of sources (Remington's 17th Ed. p. 1057).

1,3-Propanediol, 2-amino-(2-hydroxymethyl)-(tromethamine) is available commercially (Remington's 17th Ed. p. 836). It can be made by additively reacting nitromethane with formaldehyde to yield tris (hydroxymethyl) nitromethane, and the nitro compound is then hydrogenated with Raney nickel in accordance with U.S. Pat. No. 2,174,242.

3-Mercapto-1,2-propanediol (monothioglycerol) is readily made, for example, by heating an ethanolic solution of 3-chloro-1,2-propanediol with potassium bisulfite (Remington's 17th Ed. p. 1279).

The amounts of the respective components can vary fairly broadly, within conventional limits well known to those skilled in this art. Preferred embodiments will be exemplified hereinafter. Typically the folic acid salt or leucovorin salt will comprise from about 0.5 to 50 mg/ml, preferably from about 1 to about 35 mg/ml and especially preferably from about 3 to about 25 mg/ml. With folic acid sodium salt, special mention is made of 5 mg/ml and for calcium leucovorin, 3 mg/ml.

Benzyl alcohol can be omitted, but if present, can comprise up to about 2.5 percent w/v, preferably up to 1.5 percent w/v with sodium folate and up to about 0.909 percent w/v with calcium leucovorin.

The amounts of tromethamine and monothioglycerol relative to each other can vary broadly, e.g., from about 1 to 99 parts by weight, preferably from about 20 to about 80 parts by weight of the former to from about 99 to 1 parts by weight, preferably from about 80 to about 20 parts of the latter. Preferably the tromethamine and monothioglycerol each will comprise from about 0.05 percent w/v to about 0.6 percent, preferably from about 0.1 to about 0.3 percent w/v of the composition. If sodium chloride is present, it can range from 0.1 to about 1.0 percent, preferably from about 0.45 to about 0.65 percent w/v. The pH adjustors can vary widely in type and amount. Typically hydrochloric acid, 5.0 percent v/v and sodium hydroxide 4.0% w/v will be conveniently employed.

The injectable solutions prepared as described above and more fully exemplified hereinafter are used in conventional dosages. A typical daily dose is generally up to about 150 mg, e.g., in the range of from about 25 to 150 mg which is conveniently administered in divided doses, for example 2, 3 or 4 doses in a 24 hour period (methotrexate rescue with calcium leucovorin injectable). For treating folate deficiency lower doses of leucovorin are generally administered. For example, a typical daily dose for an adult human is generally in the range of 2 to 25 mg which may be conveniently administered as a single dose (leucovorin calcium) or up to 1.0 mg daily (sodium folate).

DESCRIPTION OF THE PREFERRED EMBODIMENTS

The following examples illustrate the invention but are not intended to limit the claims in any manner whatsoever.

In the data tables, the following abbreviations have the following meanings:

RT = room temperature p0 M = month
PABG = N-(p/10-aminobenzoyl)glutamic acid
FFA = folic acid)
Leucovorin Potency = leucovorin calcium (as free acid)
% LP = percent of label potency
% L. = based on label potency of leucovorin
NMT = not more than
RHC = 37° C. and 75% relative humidity in closed containers
SUN = exposure to sunlight
ND = none detected
RH = relative humidity
LCAB = light cabinet having 1,000 footcandle intensity

EXAMPLE 1

Leucovorin calcium salt is used as the active ingredient in a composition for injection having the formula set forth in Table 1:

TABLE 1

| COMPOSITION FOR INJECTION COMPRISING LEUCOVORIN CALCIUM | | |
|---|---|---|
| Ingredient | % W/V | Function in Composition |
| Leucovorin Calcium U.S.P. | 0.330* | Active Ingredient |
| Benzyl Alcohol-Reagent Grade | 0.909 | Antimicrobial Preservative |
| Tromethamine-Reagent Grade | 0.150 | Buffer |
| Monothioglycerol N.F. | 0.200 | Antioxidant |
| Sodium Chloride-Reagent Grade | 0.560 | Tonicity Adjuster |
| Hydrochloric Acid-Reagent Grade qs ad | pH 8.0–8.2 | pH Adjuster |
| Sodium Hydroxide USP qs ad | pH 8.0–8.2 | pH Adjuster |
| Water for Injection U.S.P. qs ad | 100.0 (v/v) | Vehicle |
| Nitrogen N.F., Prepurified | — | Protectant** |

*Based on Leucovorin Anhydrous Free Acid at 100%
**Used as a protective gas to retard oxidation of the product during manufacture, and as a headspace gas in the final sealed package.

The formulation is prepared as follows:

A. Production of Bulk Solution

Water for Injection, representing approximately 75% of final batch volume, is added to a stainless steel mixing tank. The Water for Injection is sparged with nitrogen until the water temperature has reached 25°–30° C. (The product is continuously sparged or blanketed with nitrogen throughout the remaining process to protect against oxidation). The ingredients are sequentially added, mixed and dissolved in the following order: benzyl alcohol; sodium chloride; tromethamine; monothioglycerol; and calcium leucovorin. The pH is then adjusted to 8.1±0.1 with 5% hydrochloric acid and/or 1% sodium hydroxide. The batch is brought to a final volume of 20–30 liters with Water for Injection sparged with nitrogen. The pH is rechecked and re-adjusted to 8.1±0.1 with hydrochloric acid or sodium hydroxide if necessary.

B. Production of Sterile Filtrate

Prior to the sterile filtration, a 0.2 micrometer filtration cartridge is tested for integrity by Bubble Point testing at a pressure of 30 psig. The bulk solution is then passed through a first stage pre-filtration unit containing an AW19/0.45 micrometer cartridge to an in-series sterile 0.2 micrometer second stage cartridge. Pump and Nitrogen gas pressure feed the solution through the filtration units to a tared sterile stainless steel collection drum. At the completion of filtration the 0.2 micrometer filtration unit is again tested for integrity by Bubble Point testing at 35 psig. Elastomeric silicone tubing is used for all product transfer.

C. Production of Filled Product

The bulk sterile solution is taken to a class 100 filling area where it is pumped from the collection drum through a sterile 5 micrometer filter to a filling line surge bottle. It is fed from the surge bottle to filling needles which eject measured doses to conveyor fed ampuls and vials. (Two filling lines, one for each package style, are used).

1 cc Amber glass ampuls are filled at 1.15±0.05 ml (1.0±0.15±0.05 ml USP overage). 10 cc Type 1 amber glass vials are filled at 10.5 ml (10.0±0.5 ml USP overage). All ampul and vial fills receive a nitrogen headspace blanket prior to sealing. Ampuls are heat sealed in a gas flame, and vials are sealed with butyl closures and aluminum crimp seals.

EXAMPLES 2 AND 3

A second batch (Example 2) corresponding to Example 1 is prepared by the method described in Example 1 as in Table 1. A third batch (Example 3) is prepared, but this is 30 liters in size instead of 20 liters, as shown in Table 1.

COMPARATIVE EXAMPLE 1A

A formulation like Example 1 without tromethamine and monothioglycerol having the formula set forth in Table 2 is included for comparison purposes:

TABLE 2

| COMPOSITION FOR INJECTION COMPRISING CALCIUM-LEUCOVORIN | | |
|---|---|---|
| Ingredient | % W/V | Function in Composition |
| Leucovorin Calcium U.S.P. | 0.270–0.330* | Active Ingredient |
| Benzyl Alcohol-Reagent Grade | 0.90 | Preservative |
| Sodium Chloride-Reagent Grade | 0.0–0.560 | Tonicity Adjuster |
| Sodium Hydroxide-N.F. qs ad | pH 7.7 ± 0.2 | pH Adjuster |
| Hydrochloric Acid-Reagent Grade qs ad | pH 7.7 ± 0.2 | pH Adjuster |
| Water for Injection U.S.P. qs ad | 100.0 (v/v) | Vehicle |
| Nitrogen N.F., Prepurified | — | Protectant** |

*Based on Leucovorin Anhydrous Free Acid at 100%.
**Used as a protective gas to retard oxidation of the product during manufacture, and as a headspace gas in the final sealed package.

The general procedure of Example 1 is used to make filled dosage forms comprising the following:

| | Batch | | | |
|---|---|---|---|---|
| Ingredient | 1A % w/v | 2A % w/v | 3A % w/v | 4A % w/v |
| Calcium Leucovorin (As Free Acid) | 0.30 | 0.27 | 0.27 | 0.33 |

-continued

| Ingredient | Batch 1A % w/v | 2A % w/v | 3A % w/v | 4A % w/v |
|---|---|---|---|---|
| Benzyl Alcohol Reagent | 0.90 | 0.90 | 0.90 | 0.90 |
| Sodium Chloride | — | — | 0.56 | 0.56 |
| Sodium Hydroxide 1.0% Solution | q.s. | q.s. | q.s. | q.s. |
| Hydrochloric Acid 1.0% Solution-Adjust to pH 7.7 | q.s. | q.s. | q.s. | q.s. |
| Water for Injection qs ad | 100 | 100 | 100 | 100 |

Amber glass ampules are the containers selected for filling.

COMPARATIVE EXAMPLES 2A, 3A and 4A

A second, third, and fourth batch of formulae without tromethamine and monothioglycerol are prepared for comparative testing using the general procedure for Example 1.

The filled dosage forms from Examples 1-3 are placed on an accelerated stability test. The analytical methodolgy is as follows:

| Analytical Methodology used for Examples 1-3 | |
|---|---|
| Test | Method |
| Description | visual |
| Leucovorin potency | High pressure liquid chromatography (HPLC) |
| Leucovorin related compounds potencies | (HPLC) |
| Benzyl Alcohol | Gas Chromatography |
| pH | pH meter |
| USP Particulate Matter | USP XXI Particulate Matter, Injections, light obscuration |
| Monothioglycerol (Identification) | Gas Chromotography |
| Microbiological evaluation of preservative system | Antimicrobial Preservative Effectiveness test USP XXI pp 1151-1156. |

The results of the test performed on he packaged formulations of Examples 1-3 are reported in Tables 3, 4 and 5, respectively:

TABLE 3

Three Month Accelerated and Six Month Room Temperature Stability Data on Leucovorin Calcium Injection Solutions 3 mg/ml (Example 1)
Amber Ampul Packaging

| Storage Condition | Leucovorin Potency % L.P. | Benzyl Alcohol % L.P. | Folic Acid % L. | PABG % L. | FFA % L. | Other Related Compounds % L. | pH | Description |
|---|---|---|---|---|---|---|---|---|
| Specification | 100-118% | 85-115% | NMT 1.0% | NMT 1.3% (1) | NMT 1.0% | NMT 2.5% (2) | 6.5-8.5 | Clear Light Yellow Solution |
| Initial | 109 | 99 | 0.25 | 0.72 | 0.35 | 1.35 | 7.93 | Clear Light Yellow Solution |
| RT, 3M | 104 | 97 | ND | 1.16 | ND | 1.91 | 7.92 | Clear Light Yellow Solution |
| RT, 6M | 105 | 97 | 0.36 | 1.56 | 0.23 | 2.18 | 7.97 | Clear Light Yellow Solution |
| RHC-1M | 105 | 95 | 0.39 | 1.50 | 0.37 | 1.82 | 7.74 | Clear Light Yellow Solution |
| RHC-2M | 104 | 97 | 0.45 | 2.24 | 0.39 | 2.80 | 7.77 | Clear Light Yellow Solution |
| RHC-3M | 102 | 94 | ND | 2.36 | ND | 2.21 | 7.90 | Clear Light Yellow Solution |
| SUN-1M | 103 | 96 | 0.39 | 1.12 | 0.23 | 2.98 | 7.78 | Clear Light Yellow Solution |
| Specification | 100-118% | 85-115% | NMT 1.0% | NMT 1.3% (1) | NMT 1.0% | NMT 2.5% (2) | 6.5-8.5 | Clear Light Yellow Solution |
| Initial | 109 | 99 | 0.25 | 0.72 | 0.35 | 1.35 | 7.93 | Clear Light Yellow Solution |
| RT, 3M | 104 | 100 | ND | 1.22 | ND | 1.49 | 7.90 | Clear Light Yellow Solution |
| RT, 6M | 105 | 97 | ND | 1.64 | 0.34 | 2.05 | 7.92 | Clear Light Yellow Solution |
| RHC-1M | 105 | 98 | 0.36 | 1.54 | 0.30 | 2.26 | 7.75 | Clear Light Yellow Solution |
| RHC-2M | 103 | 99 | ND | 2.34 | ND | 1.75 | 7.86 | Clear Light Yellow Solution |
| RHC-3M | 102 | 100 | ND | 2.59 | ND | 1.81 | 7.88 | Clear Light Yellow Solution |
| SUN-1M | 106 | 99 | 0.35 | 1.13 | 0.38 | 2.14 | 7.77 | Clear Light Yellow Solution |

(1) Not more than 1.3% for initial release and not more than 3.5% for shelf life based on the label claim of leucovorin.
(2) Not more than a sum of 2.5% for initial release and not more than 3.5% for shelf life as PABG based on the label claim of leucovorin.

TABLE 4

Three Month Accelerated and Six Month Room Temperature Stability Data on
Leucovorin Calcium Injection Solutions 3 mg/ml (Example 2)
Amber Ampul Packaging

| Storage Condition | Leucovorin Potency % L.P. | Benzyl Alcohol % L.P. | Folic Acid % L. | PABG % L. | FFA % L. | Other Related Compounds % L. | pH | Description |
|---|---|---|---|---|---|---|---|---|
| Specification | 100–118% | 85–115% | NMT 1.0% | NMT 1.3% (1) | NMT 1.0% | NMT 2.5% (2) | 6.5–8.5 | Clear Light Yellow Solution |
| Initial | 104 | 97 | 0.20 | 0.52 | 0.22 | 1.30 | 7.94 | Clear Light Yellow Solution |
| RT, 3M | 103 | 95 | ND | 0.80 | 0.18 | 1.49 | 7.90 | Clear Light Yellow Solution |
| RT, 6M | 101 | 96 | 0.27 | 1.36 | 0.25 | 1.74 | 7.97 | Clear Light Yellow Solution |
| RHC-1M | 102 | 94 | 0.05 | 1.44 | 0.31 | 2.01 | 7.76 | Clear Light Yellow Solution |
| RHC-2M | 100 | 96 | 0.40 | 2.04 | 0.28 | 2.32 | 7.91 | Clear Light Yellow Solution |
| RHC-3M | 101 | 96 | ND | 1.70 | 0.22 | 1.84 | 7.90 | Clear Light Yellow Solution |
| SUN-1M | 103 | 94 | 0.05 | 1.01 | 0.14 | 2.09 | 7.78 | Clear Light Yellow Solution |
| Specification | 100–118% | 85–115% | NMT 1.0% | NMT 1.3% (1) | NMT 1.0% | NMT 2.5% (2) | 6.5–8.5 | Clear Light Yellow Solution |
| Initial | 104 | 97 | 0.20 | 0.52 | 0.22 | 1.30 | 7.94 | Clear Light Yellow Solution |
| RT, 3M | 102 | 97 | ND | 0.93 | 0.26 | 1.91 | 7.91 | Clear Light Yellow Solution |
| RT, 6M | 102 | 97 | ND | 1.43 | 0.28 | 1.98 | 7.89 | Clear Light Yellow Solution |
| RHC-1M | 102 | 96 | 0.35 | 1.47 | 0.23 | 1.79 | 7.74 | Clear Light Yellow Solution |
| RHC-2M | 100 | 97 | ND | 2.12 | ND | 1.63 | 7.87 | Clear Light Yellow Solution |
| RHC-3M | 101 | 98 | 0.25 | 2.03 | 0.32 | 2.21 | 7.86 | Clear Light Yellow Solution |
| SUN-1M | 103 | 96 | 0.36 | 1.05 | 0.28 | 2.00 | 7.76 | Clear Light Yellow Solution |

(1) Not more than 1.3% for initial release and not more than 3.5% for shelf life based on the label claim of leucovorin.
(2) Not more than a sum of 2.5% for initial release and not more than 3.5% for shelf life as PABG based on the label claim of leucovorin.

TABLE 5

Three Month Accelerated and Six Month Room Temperature Stability Data on
Leucovorin Calcium Injection Solutions 3 mg/ml (Example 3)
Amber Ampul Packaging

| Storage Condition | Leucovorin Potency % L.P. | Benzyl Alcohol % L.P. | Folic Acid % L. | PABG % L. | FFA % L. | Other Related Compounds % L. | pH | Description |
|---|---|---|---|---|---|---|---|---|
| Specification | 100–118% | 85–115% | NMT 1.0% | NMT 1.3% (1) | NMT 1.0% | NMT 2.5% (2) | 6.5–8.5 | Clear Light Yellow Solution |
| Initial | 108 | 100 | 0.46 | 0.68 | 0.27 | 1.04 | 8.09 | Clear Light Yellow Solution |
| RT, 3M | 108 | 101 | 0.44 | 1.02 | 0.08 | 1.47 | 7.98 | Clear Light Yellow Solution |
| RT, 6M | 103 | 99 | 0.66 | 1.36 | ND | 1.78 | 8.00 | Clear Light Yellow Solution |
| RHC-1M | 107 | 98 | 0.49 | 0.89 | 0.15 | 1.81 | 7.95 | Clear Light Yellow Solution |
| RHC-2M | 105 | 101 | 0.54 | 0.96 | 0.26 | 2.24 | 7.96 | Clear Light Yellow Solution |
| RHC-3M | 108 | 99 | 0.52 | 1.08 | 0.10 | 1.55 | 8.00 | Clear Light Yellow Solution |
| SUN-1M | 107 | 98 | 0.49 | 0.88 | 0.15 | 1.80 | 7.96 | Clear Light Yellow Solution |
| Specification | 100–118% | 85–115% | NMT 1.0% | NMT 1.3% (1) | NMT 1.0% | NMT 2.5% (2) | 6.5–8.5 | Clear Light Yellow Solution |
| Initial | 108 | 100 | 0.46 | 0.68 | 0.27 | 1.04 | 8.09 | Clear Light Yellow Solution |
| RT, 3M | 107 | 98 | 0.54 | 1.16 | 0.12 | 1.51 | 7.96 | Clear Light Yellow Solution |
| RT, 6M | 103 | 98 | 0.92 | 1.41 | 0.34 | 1.88 | 8.00 | Clear Light Yellow Solution |
| RHC-1M | 107 | 98 | 0.48 | 0.96 | 0.24 | 1.41 | 7.95 | Clear Light Yellow Solution |
| RHC-2M | 106 | 100 | 0.52 | 1.01 | 0.23 | 1.94 | 7.96 | Clear Light Yellow Solution |

TABLE 5-continued

Three Month Accelerated and Six Month Room Temperature Stability Data on
Leucovorin Calcium Injection Solutions 3 mg/ml (Example 3)
Amber Ampul Packaging

| Storage Condition | Leucovorin Potency % L.P. | Benzyl Alcohol % L.P. | Folic Acid % L. | PABG % L. | FFA % L. | Other Related Compounds % L. | pH | Description |
|---|---|---|---|---|---|---|---|---|
| RHC-3M | 108 | 101 | 0.47 | 1.10 | 0.10 | 1.50 | 7.98 | Clear Light Yellow Solution |
| SUN-1M | 105 | 99 | 0.51 | 0.98 | 0.17 | 1.48 | 7.96 | Clear Light Yellow Solution |

(1) Not more than 1.3% for initial release and not more than 3.5% for shelf life based on the label claim of leucovorin.
(2) Not more than a sum of 2.5% for initial release and not more than 3.5% for shelf life as PABG based on the label claim of leucovorin.

The effectiveness of the preservative system of this invention for Leucovorin Calcium Injectable Solutions, Examples 1-3, is tested in accordance with the Antimicrobial Preservatives Effectiveness Test outlined in U.S. Phamacopeia XXI, pages 1151-1156. This provides a measure of the capacity of the solutions to decrease microbial growth when individually challenged with *Staphylococcus aureus*, *Escherichia coli*, *Psuedomonas aeruginusa*, *Candida albicans* and *Aspergillus niger* at a dose level of 100,000 to 1,000,000 microorganisms per ml. The contaminated solutions are stored and sampled at a series of time intervals in order to obtain microorganism counts. The results of these tests, set forth in Tables 6, 7 and 8, indicate that the benzyl alcohol prevents the growth of microorganisms, and provides qualities necessary to pass the *anti-microbial preservative effectiveness test*.

TABLE 6

Microbiological Evaluation of Preservative System -
U.S.P. XXI Method
Example 1

| Organism | Inoculation Count | 1 Week | 2 Weeks | 3 Weeks | 4 Weeks |
|---|---|---|---|---|---|
| Staphylococcus aureus | 108,500 | <10 | <10 | <10 | <10 |
| Escherichia coli | 108,500 | <10 | <10 | <10 | <10 |
| Psuedomonas aeruginosa | 105,500 | <10 | <10 | <10 | <10 |
| Candida albicans | 285,000 | 5,800 | <10 | <10 | <10 |
| Aspergillus niger | 610,000 | 1,900 | <10 | <10 | <10 |

TABLE 7

Microbiological Evaluation of Preservative System -
U.S.P. XXI Method
Example 2

| Organism | Inoculation Count | 1 Week | 2 Weeks | 3 Weeks | 4 Weeks |
|---|---|---|---|---|---|
| Staphylococcus aureus | 108,500 | <10 | <5 | <10 | <10 |
| Escherichia coli | 108,500 | 5 | <10 | <10 | <10 |
| Psuedomonas aeruginosa | 105,500 | <10 | <10 | <10 | <10 |
| Candida albicans | 285,000 | 9,300 | <10 | <10 | <10 |
| Aspergillus niger | 610,000 | 2,000 | <10 | <10 | <10 |

TABLE 8

Microbiological Evaluation of Preservative System -
U.S.P. XXI Method
Example 3

| Organism | Inoculation Count | 1 Week | 2 Weeks | 3 Weeks | 4 Weeks |
|---|---|---|---|---|---|
| Staphylococcus aureus | 108,500 | <10 | <10 | 5 | <10 |
| Escherichia coli | 108,500 | <10 | <10 | <10 | <10 |
| Psuedomonas aeruginosa | 105,500 | <10 | <10 | <10 | <10 |
| Candida albicans | 285,000 | 9,550 | <10 | <10 | <10 |
| Aspergillus niger | 610,000 | 190 | <10 | <10 | <10 |

The storage stability and microbiological testing of the injectable leucovorin calcium preparations set forth under Comparative Examples 1A, 1B, 1C and 1D using standard test methods are determiend by the following procedures:

| Test | Method |
|---|---|
| Description | Visual |
| Leucovorin potency | Thin layer Chromatography |
| Benzyl Alcohol | Spectrophotometric Gas Liquid Chromatography |
| pH | pH meter |
| Microbiological evaluation of preservative system | Antimicrobial Effectiveness Test USP XIX page 587 |

Stability data for the comparison calcium injection compositions are set forth in Tables 9, 10 and 11:

TABLE 9

MEAN ASSAY YIELDS, EXPRESSED AS PERCENT
LABEL POTENCY FOR LEUCOVORIN CALCIUM (AS FREE ACID)

| | Example | | | |
|---|---|---|---|---|
| | 1A % LP | 2A % LP | 3A % LP | 4A % LP |
| Label Potency (In mg) of Leucovorin | 3.0 | 2.7 | 2.7 | 3.0 |
| Theory | 100 | 100 | 100 | 110 |
| Initial | 99 | 97 | 105 | 107 |
| 70° C., 1W | 89 | — | — | 103 |
| 70° C., 2W | 84 | — | — | 99 |
| 56° C., 2W | 92 | — | — | 105 |
| 56° C., 1M | 89 | — | — | 101 |
| 56° C., 2M | 86 | — | — | 99 |
| 42° C., 1M | 94 | — | — | 106 |
| 42° C., 2M | 94 | 92 | 94 | 107 |
| 42° C., 4M | — | 89 | 83 | 98 |
| 42° C., 5M | 92 | — | — | — |
| RT, 3M | — | 97 | 98 | — |
| RT, 4M | — | — | 102 | — |
| RT, 6M | 97 | 95 | 97 | — |
| RT, 7M | 96 | — | — | 106 |
| RT, 9M | — | — | — | 107 |
| RT, 10M | 96 | — | 96 | — |
| RT, 11M | — | 98 | — | — |
| RT, 13M | — | 97 | 99 | — |

TABLE 9-continued

MEAN ASSAY YIELDS, EXPRESSED AS PERCENT LABEL POTENCY FOR LEUCOVORIN CALCIUM (AS FREE ACID)

| | Example | | | |
|---|---|---|---|---|
| | 1A % LP | 2A % LP | 3A % LP | 4A % LP |
| RT, 16M | — | — | — | 99 |
| RT, 22M | 94 | — | — | — |
| RT, 29M | — | 91 | — | — |
| RT, 30M | — | — | 96 | — |
| Sun 1M | — | — | 97 | 100 |

TABLE 10

MEAN ASSAY YIELDS, EXPRESSED AS PERCENT LABEL POTENCY FOR BENZYL ALCOHOL

| | Example | | | |
|---|---|---|---|---|
| | 1A % LP | 2A % LP | 3A % LP | 4A % LP |
| Label Potency (In mg) | 9.0 | 9.0 | 9.0 | 9.0 |
| Theory | 100 | 100 | 100 | 100 |
| Initial | 101 | 98 | 101 | 101 |
| 70° C., 1W | 126 | — | — | 109 |
| 70° C., 2W | 94 | — | — | 100 |
| 56° C., 2W | 106 | — | — | 102 |
| 56° C., 1M | — | — | — | 102 |
| 56° C., 2M | — | — | — | 99 |
| 42° C., 1M | 97 | — | — | 95 |
| 42° C., 2M | 99 | 101 | 102 | 99 |
| 42° C., 4M | — | 83 | — | 98 |
| RT, 3M | — | 100 | — | — |
| RT, 4M | — | — | — | 99 |
| RT, 6M | 98 | 87 | — | — |
| RT, 7M | 99 | 93 | — | 99 |
| RT, 8M | — | — | 101 | 98 |
| RT, 9M | 101 | — | — | — |
| RT, 10M | 82 | — | 102 | — |
| RT, 11M | 101 | 97 | — | — |
| RT, 13M | — | — | 102 | — |
| RT, 14M | — | 101 | — | — |
| RT, 16M | — | — | — | 106 |
| RT, 21M | — | 97 (a) | — | — |
| RT, 24M | 101 | — | — | — |
| RT, 25M | 101 (a) | — | — | — |
| RT, 27M | — | 113 (a) | — | — |
| RT, 29M | — | 105 (a) | — | — |
| RT, 30M | — | — | 105 (a) | — |
| Sun, 1M | — | — | 101 | 100 |

(a) Gas-liquid chromatography is used for these assays and for all the assays in Example 4A. All the other assay data are derived using spectrophotometric method of analysis. The assay results using the spectrophotometric method of analysis are quite variable due to analytical interferences.

TABLE 11

ELECTROMETRIC pH DETERMINATIONS AT AMBIENT TEMPERATURE

| | pH Value Example | | | |
|---|---|---|---|---|
| | 1A | 2A | 3A | 4A |
| Initial | 7.7 | 7.7 | 7.7 | 7.7 |
| RT, 2M | — | 6.6 | — | 6.5 |
| RT, 4M | — | 7.0 | — | — |
| RT, 6M | 6.8 | — | — | 6.6 |
| RT, 9M | 6.4 | — | 6.8 | — |
| RT, 12M | — | — | — | 6.5 |
| RT, 24M | — | 6.7 | — | — |
| RT, 28M | — | — | 7.0 | — |
| RT, 29M | — | 6.5 | — | — |
| RT, 32M | — | — | — | 6.4 |
| RT, 34M | 6.6 | — | — | — |
| RT, 36M | — | — | — | 6.2 |

The effectiveness of the preservative system of Leucovorin Calcium Injectable Solutions, for Comparative Examples 1A, 2A, 3A, and 4A is tested in accordance with the Antimicrobial Preservatives Effectiveness Test outlined measure of the capacity of the solutions to decrease microbial growth when individually challenged with Staphylococcus aureus, Escherichia coli, Psuedomonas aeruginusa, Candid albicans and Aspergillus niger at a dose level of 100,000 to 1,000,000 microorganisms per ml. The contaminated solutions are stored and sampled at a series of time intervals in order to obtain microorganism counts. The results of these tests are set forth in Table 12.

TABLE 12

Microbiological Evaluation of Preservative System - U.S.P. XIX Method

| | Inoculation Count | 0.5 Hour | 24 Hours | 1 Week | 2 Weeks | 4 Weeks |
|---|---|---|---|---|---|---|
| Example 1A | | | | | | |
| Staphylococcus aureus | 270,000 | 202,000 | <1,000 | <100 | <100 | <100 |
| Escherichia coli | 245,000 | 32,000 | <1,000 | <100 | <100 | <100 |
| Psuedomonas aeruginosa | 59,000 | <1,000 | <100 | <100 | <100 | |
| 410,000 | | | | | | |
| Candida albicans | 330,000 | 130,000 | <4,000 | <100 | <100 | <100 |
| Aspergillus niger | 120,000 | 340,000 | 230,000 | 57,000 | 1,000 | <100 |
| Example 2A | | | | | | |
| Staphylococcus aureus | 205,000 | 63,000 | <1,000 | <100 | <100 | <100 |
| Escherichia coli | 180,000 | 55,000 | <1,000 | <100 | <100 | <100 |
| Psuedomonas aeruginosa | 210,000 | 21,000 | <100 | <100 | <100 | <100 |
| Candida albicans | 154,000 | 61,000 | 48,500 | <100 | <100 | <100 |
| Aspergillus niger | 280,000 | 26,000 | 270,000 | 29,000 | 1,800 | <100 |
| Example 3A | | | | | | |
| Staphylococcus aureus | 270,000 | <1,000 | <1,000 | <100 | <100 | <100 |
| Escherichia coli | 200,000 | <1,000 | <1,000 | <100 | <100 | <100 |
| Psuedomonas aeruginosa | 314,000 | <1,000 | <1,000 | <100 | <100 | <100 |
| Candida albicans | 78,000 | <1,000 | <1,000 | <100 | <100 | <100 |
| Aspergillus niger | 210,000 | <200 | 100,000 | <50 | <100 | <100 |
| Example 4A | | | | | | |
| Staphylococcus aureus | 257,000 | 160,000 | <100 | <100 | <100 | <100 |
| Escherichia coli | 238,000 | 194,000 | 20,000 | <100 | <100 | <100 |
| Psuedomonas aeruginosa | 340,000 | 97,000 | <100 | <100 | <100 | <100 |
| Candida albicans | 114,000 | 92,000 | <100 | <100 | <100 | <100 |

TABLE 12-continued

| Microbiological Evaluation of Preservative System - U.S.P. XIX Method | | | | | | |
|---|---|---|---|---|---|---|
| | Inoculation Count | 0.5 Hour | 24 Hours | 1 Week | 2 Weeks | 4 Weeks |
| *Aspergillus niger* | 380,000 | 330,000 | 440,000 | 160,000 | 950 | <100 |

EXAMPLES 4, 5 AND 6

Three batches are prepared with leucovorin calcium salt as the active ingredient in a composition for injection having the formula set forth in Table 13:

TABLE 13

| COMPOSITION FOR INJECTION COMPRISING LEUCOVORIN CALCIUM | | |
|---|---|---|
| Ingredient | % W/V | Function in Composition |
| Leucovorin Calcium U.S.P. | 1.100 | Active Ingredient |
| Tromethamine-Reagent Grade | 0.150 | Buffer |
| Monothioglycerol N.F. | 0.200 | Antioxidant |
| Sodium Chloride-Reagent Grade | 0.560 | Tonicity Adjuster |
| Hydrochloric Acid-Reagent Grade qs ad | pH 7.9–8.3 | pH Adjuster |
| Sodium Hydroxide USP qs ad | pH 7.9–8.3 | pH Adjuster |
| Water for Injection U.S.P. qs ad | 100.0 (v/v) | Vehicle |
| Nitrogen N.F., Prepurified | — | Protectant** |

*Based on Leucovorin Anhydrous Free Acid at 100%
**Used as a protective gas to retard oxidation of the product during manufacture, and as a headspace gas in the final sealed package.

The resulting composition is a clear light yellow solution. Each batch is 40 liters. The solutions are then distributed to 50 ml amber tubing vials with 50 mg/vial label potency. Grey butyl plug closures are used with aluminum seals.

The filled dosage forms from Examples 4, 5 and 6 are placed on accelerated stability tests, consisting of storing the solution at 23° C. for up to 9 months, storing the solution at 40° C. and at 75% relative humidity for up to three months, and storing the solution for one month in a light cabinet.

The solutions are assayed by high performance liquid chromatography. The mean assay results of the tests performed on the packaged formulations of Examples 4, 5 and 6 are reported in Table 14:

TABLE 14

| Mean Assay Results For Leucovorin Calcium Injection Solutions 500 mg/vial (Examples 4, 5 and 6) | | | | |
|---|---|---|---|---|
| | | Example No. | | |
| Storage Condition | Time | 4 % L.P. | 5 % L.P. | 6 % L.P. |
| Initial | | 110 | 106 | 109 |
| 23° C. | 3M | 106 | 104 | 106 |
| 23° C. | 6M | 107 | 105 | 106 |
| 23° C. | 9M | 106 | 104 | 105 |
| 23° C. | 12M | 103 | 102 | 104 |
| 40° C./75% RH | 1M | 102 | 101 | 101 |
| 40° C./75% RH | 2M | 99 | 98 | 100 |
| 40° C./75% RH | 3M | 98 | 97 | 99 |
| LCAB* | 1M | 107 | 105 | 106 |

The packaged formulations of Examples 4, 5 and 6 did not change in appearance after being stored at 23° C. for up to 9 months, 40° C. and 75% relative humidity for up to three months, and in a light cabinet for one month. The compositions remained clear light yellow solutions.

The solutions of Examples 4, 5 and 6 are measured electrometrically for pH. The results of these tests, showing that the pH remained essentially unchanged at all storage conditions, are reported in Table 15:

TABLE 15

| pH Measurement Data For Leucovorin Calcium Injection Solutions 500 mg/vial (Examples 4, 5 and 6) | | | | |
|---|---|---|---|---|
| | | Example No. | | |
| Storage Condition | Time | 4 pH | 5 pH | 6 pH |
| Initial | | 8.2 | 8.4 | 8.4 |
| 23° C. | 3M | 8.1 | 8.2 | 8.3 |
| 23° C. | 6M | 8.0 | 8.1 | 8.2 |
| 23° C. | 9M | 8.1 | 8.3 | 8.4 |
| 23° C. | 12M | 8.1 | 8.2 | 8.3 |
| 40° C./75% RH | 1M | 8.2 | 8.4 | 8.4 |
| 40° C./75% RH | 2M | 8.0 | 7.9 | 8.1 |
| 40° C./75% RH | 3M | 8.0 | 8.0 | 8.1 |

EXAMPLE 5

If the procedure of Example 1 is repeated substituting sodium folate for the calcium leucovorin, using the following ingredients: sodium folate equivalent to 5 mg of folic acid; disodium edetate 0.2%; Water for Injection; q.s. 100%; sodium hydroxide to approximately pH 9; benzyl alcohol; 1.5%; tromethamine, 0.15%; and monothioglycerol, 0.200%, all percentages by weight over volume, a stable injectable composition in accordance with this invention will be obtained.

The foregoing data indicate that a unique blend of a buffer and an antioxidant endows leucovorin with more stability than the present standard formulation of leucovorin (Comparative Examples). More particularly, the composition of this invention is shown to be:

(1) a formulation which is more stable than the present standard product system in terms of pH: with variations of no more than 0.4 pH units from an adjusted pH of 8.1, and thus provides a stabilized alkaline pH to insure maximum stability of leucovorin calcium;

(2) a formulation with better leucovorin potency photostability after one month exposure to sunlight when compared to the standard product formulation;

(3) a formulation which has equivalent or better leucovorin potency stability overall;

(4) a formulation with equivalent benzyl alcohol potency stability, as compared to the standard product formulation.

(5) a formulation where the generation of related compounds does not exceed the specified limits for the standard product formulation;

(6) a formulation which meets the present Antimicrobial Preservatives Effectiveness test as outlined in U.S.P. XXI; and (7) a formulation which has a projected expiration dating of at least eighteen months.

The above-mentioned patents, publications and test methods are incorporated herein by reference.

The foregoing detailed description will suggest many obvious variations to those skilled in this art. For example, instead of calcium leucovorin, strontium leucovorin and sodium leucovorin can be used. Racemic and enantiomeric 1-leucovorin can be used. Benzyl alcohol can be omitted. Instead of sodium folate, calcium folate can be used. Derivatives, such as polyglutamyl folates and leucovorin can be used. The injectable compositions can contain conventional additives such as chelating agents, inert gases, and the like. All such obvious modifications are within the full intended scope of the appended claims.

I claim:

1. A stable, injectable aqueous composition comprising:
   (i) an effective amount of from about 0.5 mg/ml to about 50 mg/ml of a water soluble pharmaceutically-acceptable salt of folic acid or leucovorin;
   (ii) optionally, an effective preservative amount of from about 0.0% w/v to about 2.5% w/v of benzyl alcohol; and
   (iii) an effective amount of a buffer/antioxidant combination consisting essentially of
      (a) tromethamine and
      (b) monothioglycerol, said
   combination (iii) being present in an amount at least sufficient to maintain the pH of said composition in a predetermined range of from about 6 to about 10 and to protect the composition against degradation induced by oxygen or light wherein said tromethamine and said monothioglycerol are each present in an amount from about 0.5% w/v to about 6.0% w.v.

2. A composition as defined in claim 1 wherein said salt comprises a salt of leucovorin.

3. A composition as defined in claim 1 which also includes
   (iv) sodium chloride in an amount sufficient to render said composition isotonic.

4. A composition as defined in claim 1 which also includes
   (v) a pH adjustor comprising an acid or a base in an amount sufficient to adjust the pH to any value within said range.

5. A composition as defined in claim 4 wherein said pH adjustor comprises hydrochloric acid or sodium hydroxide.

6. A composition as defined in claim 2 wherein said leucovorin salt comprises calcium leucovorin.

7. A pharmaceutical formulation comprising from 3 mg/ml to 25 mg/ml of Leucovorin Calcium in an isotonic solution at a pH of from 6.5 to 8.5, with or without benzyl alcohol at a concentration of from 0.0% w/v to 0.909% w/v, TRIS (tromethamine) at a concentration of from 0.10% w/v to 0.30% w/v, monothioglycerol at a concentration of from 0.10% w/v to 0.30% w/v; sodium chloride at a concentration from 0.45% to 0.65% w/v, with hydrochloric acid at a concentration of 5.0 v/v% to 10.0 v/v % and sodium hydroxide at a concentration of 1.0 w/v % to 5.0 w/v % added as required to adjust the pH.

8. A formulation according to claim 7, where the concentration of Leucovorin Calcium is from 3.0 mg to 3.54 mg/ml and the concentrations of benzyl alcohol, TRIS (tromethamine), monothioglycerol and sodium chloride are from 0.765% w/v to 1.035% w/v, 0.150% w/v, 0.200% w/v and 0.560% w/v, respectively.

9. A formulation according to claim 7, where the concentration of Leucovorin Calcium is 10.0 to 11.0 mg/ml and the concentrations of TRIS (tromethamine), monothioglycerol and sodium chloride are 0.150% w/v, 0.200% w/v and 0.560% w/v, respectively.

10. A method for stabilizing an injectable aqueous composition against deterioration, said method comprising:
   A. providing an aqueous composition comprising
      (i) an effective amount of from about 0.5 mg/ml to about 50 mg/ml of a water-soluble pharmaceutically acceptable salt of folic acid or leucovorin;
      (ii) optionally, a small effective preservative amount of from about 0.0% w/v to about 2.5% w/v of benzyl alcohol, and
   B. adding thereto
      (iii) an effective amount of a buffer/antioxidant combination consisting essentially of
         (a) tromethamine and
         (b) monothioglycerol, said
   combination (iii) being provided in an amount at least sufficient to maintain the pH of said composition in a predetermined range of from about 6 to about 10 and to protect the composition against degradation induced by oxygen and light wherein said tromethamine and said monothioglycerol are each present in an amount from about 0.5% w/v to about 6.0% w/v.

11. A method as defined in claim 10 wherein said salt comprises a salt of leucovorin.

12. A method for stabilizing an injectable aqueous composition as defined in claim 10, including the step of
   (C) adding thereto
      (iv) sodium chloride in an amount sufficient to render said composition isotonic.

13. A method for stabilizing an injectable aqueous composition as defined in claim 10, also including the step of
   (D) adding thereto
      (v) a pH adjustor comprising a acid or a base in amount sufficient to adjust the pH to any value within said range.

14. A method for stabilizing an injectable aqueous composition as defined in claim 13, wherein said pH adjustor comprises hydrochloric acid or sodium hydroxide.

15. A method for stabilizing an injectable aqueous composition as defined in claim 11, wherein said leucovorin salt comprises calcium leucovorin.

16. A method for stabilizing a pharmaceutical formulation comprising providing from 3 mg/ml to 25 mg/ml of Leucovorin Calcium in an isotonic solution at a pH of from 6.5 to 8.5, with or without benzyl alcohol at a concentration of from 0.0% w/v to 0.909% w/v, and adding thereto TRIS (tromethamine) at a concentration from 0.10% w/v to 0.30% w/v, monothioglycerol at a concentration of from 0.10% w/v to 0.30% w/v; sodium chloride at a concentration of from 0.45% w/v to 0.65% w/v, and sufficient hydrochloric acid at a concentration of 5.0 v/v% to 10.0 v/v% and sodium hydroxide at a concentration of 1.0 w/v% to 5.0% w/v added as needed to adjust the pH.

17. A method for stabilizing a formulation according to claim 16, where the concentration of Leucovorin Calcium is from 3.0 mg to 3.54 mg/ml and the concentrations of benzyl alcohol, TRIS (tromethamine), monothioglycerol and sodium chloride are from 0.765% w/v to 1.035% w/v, 0.150% w/v, 0.200% w/v and 0.560% w/v, respectively.

18. A method for stabilizing a formulation according to claim 16, where the concentration of Leucovorin Calcium is 10.0 to 11.0 mg/ml and the concentrations of TRIS (tromethamine), monothioglycerol and sodium chloride are 0.150% w/v, 0.200% w/v and 0.560% w/v, respectively.

19. A composition as defined in claim 2, wherein said salt comprises a salt of dl-leucovorin.

20. A composition as defined in claim 2, wherein said salt comprises a salt of l-leucovorin.

* * * * *